US006261431B1

(12) United States Patent
Mathies et al.

(10) Patent No.: US 6,261,431 B1
(45) Date of Patent: Jul. 17, 2001

(54) PROCESS FOR MICROFABRICATION OF AN INTEGRATED PCR-CE DEVICE AND PRODUCTS PRODUCED BY THE SAME

(75) Inventors: Richard A. Mathies; Peter C. Simpson; Stephen J. Williams, all of Berkeley, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/221,436

(22) Filed: Dec. 28, 1998

(51) Int. Cl.[7] .................. G01N 27/26; G01N 27/447; C12M 1/40

(52) U.S. Cl. .................. 204/601; 204/450; 204/451; 204/453; 204/600; 204/601; 435/286.1; 435/287.2; 435/303.1

(58) Field of Search .................. 204/450, 451, 204/452, 453, 454, 455, 600, 601, 602, 603, 604, 605; 435/286.1, 287.2, 303.1

(56) References Cited

U.S. PATENT DOCUMENTS

| 4,821,997 | 4/1989 | Zdeblick | 251/11 |
| 4,965,188 | 10/1990 | Mullis et al. | 435/6 |
| 5,006,749 | 4/1991 | White | 310/323.03 |

(List continued on next page.)

FOREIGN PATENT DOCUMENTS

| 9015070 | 12/1990 | (WO) . |
| 9210092 | 6/1992 | (WO) . |
| 9405414 | 3/1994 | (WO) . |
| 9712063 | 3/1997 | (WO) . |
| WO 97/12063 | * 4/1997 | (WO) . |

OTHER PUBLICATIONS

Wade, N., "Meeting of Computers and Biology: The DNA Chip," Apr. 8, 1997, Science Times, The New York Times, N. Y. Times News Service.

Woolley, A. T., Hadley, D., Landre, P., deMello, A. J., Mathies, R. A. and Northrup, M.A., 1996, 68 Analytical Chemistry 4081–4086.

Waters, L. C., Jacobson, S. C., Kroutchinina, N., Khandurina, J., Foote, R. S. and Ramsey, J. M., 1998, 70 (1) Anal. Chem. 158–162.

(List continued on next page.)

*Primary Examiner*—Jill Warden
*Assistant Examiner*—John S. Starsiak, Jr.
(74) *Attorney, Agent, or Firm*—Pillsbury Winthrop LLP

(57) ABSTRACT

A fully integrated monolithic small volume PCR-CE device in glass, or the like materials, is fabricated using thin film metal heaters and thermocouples to thermally cycle submicroliter PCR volumes. Successful amplification of a PCR fragment is demonstrated on a PCR-CE chip. The process utilizes a linear polyacrylamide surface coating coupled with addition of BSA to the amplification buffer was necessary to obtain amplification efficiencies comparable to a positive control. The micro-reactor reduced significantly the time required for amplification and the reaction volume was in the sub-microlitre regime. Likewise addressed are the known problems connected with reliable microfabrication of metal coatings and the insulating layers required to shield these layers from the PCR reaction mix, and the longstanding unresolved issue of exposed metal regions in the PCR-CE chip resulting in electrolysis of water and bubble formation whenever a voltage is applied. The instant teachings employ external heaters and thermocouples and, as such, have alleviated many of these problems. Heaters and thermocouples may still be thin film deposited after chip bonding allowing for easy scale-up to multichannel devices. In addition, direct deposition of these chip components insures good thermal contact with the PCR reactor.

29 Claims, 11 Drawing Sheets

U.S. PATENT DOCUMENTS

| | | |
|---|---|---|
| 5,143,854 | 9/1992 | Pirrung et al. .................... 436/518 |
| 5,241,363 | 8/1993 | Garner .............................. 356/326 |
| 5,252,294 | 10/1993 | Kroy et al. ......................... 422/102 |
| 5,296,374 | 3/1994 | Culshaw et al. ................ 435/287.9 |
| 5,304,487 | 4/1994 | Wilding et al. ..................... 435/29 |
| 5,384,261 | 1/1995 | Winkler et al. .................... 436/518 |
| 5,498,392 | 3/1996 | Wilding et al. ................... 422/68.1 |
| 5,544,276 | 8/1996 | Loux et al. ........................ 392/480 |
| 5,554,276 | 9/1996 | Kozak et al. ........................ 210/87 |
| 5,585,069 | 12/1996 | Zanzucchi et al. ............. 204/450 X |
| 5,593,838 | 1/1997 | Zanzucchi et al. ............. 204/450 X |
| 5,603,351 | 2/1997 | Cherukuri et al. ............. 204/600 X |
| 5,632,876 | 5/1997 | Zanzucchi et al. ................ 204/600 |
| 5,643,738 | 7/1997 | Zanzucchi et al. .................... 435/6 |
| 5,681,484 | 10/1997 | Zanzucchi et al. ..................... 216/2 |
| 5,824,204 * | 10/1998 | Jerman .............................. 204/601 |
| 5,849,208 * | 12/1998 | Hayes et al. ......................... 216/94 |

OTHER PUBLICATIONS

Woolley, A. T. and Mathies, R. A., 1994, 91 PNAS 11348–11352; Simpson, P.C., Woolley, A. T. and Mathies, R. A., 1998 95 Proc. Nal. Acad. Sci. USA. 2256–2261.

Fodor et al., Science, 251:767–777 (1991).

Woolley and Mathies, Proc. Nat'l Acad. Sci. USA (1994) 91:11348–11352.

Jacobsen, et al., Anal. Chem. (1994 66:1114–1118, Effenhauser, et al., Anal chem. (1994) 66:2949–2953, Harrison, et al. Science (1993) 261:895–897, Effenhauser, et al. Anal. Chem. (1993) 65:2637–2642, and Manz, et al., J. Chromatog. (1992) 593:243–258.

Brenner, et al., Proc. Nat'l Acad. Sci. (1989) 86:8902–8906.

\* cited by examiner

PROCESS FOR MICROFABRICATION OF AN INTEGRATED PCR-CE DEVICE AND PRODUCTS PRODUCED BY THE SAME

This work was supported in part by a NIST ATP grant to Affymetrix, Incorporated which has been used in conjunction with the Department of Chemistry of the University of California at Berkeley, and the Molecular Dynamics Company.

BACKGROUND OF THE INVENTION

1. Area of the Art

The present invention relates to methods and apparatus for assaying biomolecular characteristics and structural configurations effective for use within the context of microfluidic loading and transfer methods. Particularly, the present invention relates to novel enhanced techniques for the facilitation of fabrication and improvement of microapparatus including the development of a microfabricated PCR reactor that is integrated on a CE chip, inter alia.

2. Description of the Prior Art

The "DNA Chip" has been heralded as the long awaited union between contemporary microelectronic technology and the genetic engineering arts. (Wade, N., "Meeting of Computers and Biology: The DNA Chip", Apr. 8, 1997, Science Times, *THE NEW YORK TIMES*, N.Y. Times New Service). The present invention constitutes another aspect of the innovative cycle which was both the genesis of contemporary 'gene chip' technology and a prominent candidate for its most utile application to date.

The Polymerase Chain Reaction ("PCR") is a powerful procedure for amplifying and labeling long stretches of DNA using chromosomal or plasmid DNA as well as labeled nucleotides, those skilled in the art define the same as an in vitro technique for rapidly synthesizing large quantities of a given DNA segment that involves separating the DNA into its two complementary strands, binding a primer to each single strand at the end of the given DNA segment where synthesis will start, using DNA polymerase to synthesize two-stranded DNA from each single strand, and repeating the process.

Likewise, Capillary Electrophoresis ("CE") is a method of using silica capillaries to separate a wide variety of solutes, both charged and uncharged, and having particularly effective uses for the separation of small peptides, proteins and the like biomolecular moieties, as in the case of the instant teachings.

By way of background, attention is called to co-pending U.S. Ser. No. 08/535,875; filed Sep. 28, 1995, which is assigned a common assignee, and was likewise invented by one of the present inventors. The '875 app. is incorporated in its entirety herein by reference, and provides valuable insight into the state of the art.

Generic schemata which likewise comprise basic reactor designs, including miniature temperature controlled reaction chambers for carrying out a variety of synthetic and diagnostic applications, for tasks from sizing of nucleic acids for hybridization, chemical labeling, thermal cycling, nucleic acid fragmentation, sizing and transcription all of the way to rudimentary sequencing were disclosed by the '875 app.

A large number of diagnostic and synthetic chemical reactions require repeated cycling through a number of specific temperatures to carry out the melting, annealing, and ligation or extension steps which are part of the respective processes. By reducing reaction volumes, the amount of time required for thermal cycling may also be reduced, thereby accelerating the amplification process. Further, this reduction in volume also results in a reduction of the amounts of reagents and sample used, thereby decreasing costs and facilitating analyses of increasingly smaller amounts of material.

Similarly, in hybridization applications, precise temperature controls likewise are used to obtain optimal hybridization conditions. Finally, a number of other pre- and post-hybridization treatments also require some degree of precise temperature control, such as fragmentation, transcription, chain extension for sequencing, labeling, ligation reactions, and the like.

A number of researchers have attempted to miniaturize and integrate reaction vessels for carrying out a variety of chemical reactions, including nucleic acid manipulation. For example, published PCT Application No. WO 94/05414, to Northrup and White reports an integrated micro-PCR apparatus fabricated from thin silicon wafers, for collection and amplification of nucleic acids from a specimen. Similarly, U.S. Pat. No. 5,304,487 to Wilding, et al., and U.S. Pat. No. 5,296,374 to Kricka, et al. discuss chambers and flow channels micromachined from silicon substrates for use in conjunction with the collection and analysis of cell samples. However, neither of these references address the added constraints of PCR, and how to protect adequately against the same.

The increased desire for automated chemical processes in both analytical and synthetic applications has led to a need for further miniaturization and integration of existing processes and equipment for carrying out such processes.

For miniaturized DNA analysis the successful and reliable coupling of PCR amplification and electrophoretic DNA separation constitutes a particularly noteworthy and certainly laudable aspiration. Integration of such techniques offers numerous potential advantages in terms of speed, cost and automation. Multiple reactors and separation channels have been envisaged by artisans as part of a high throughput genetic analysis system. The first effort which has become generally accepted among the technical community as a reasonable attempt at a substantially integrated PCR reactor on a CE chip was the hybrid device reported by Woolley and coworkers in 1996 (Woolley, A. T., Hadley, D., Landre, P., deMello, A. J., Mathies, R. A. and Northrup, M A., 1996, 68 *Analytical Chemistry* 4081–4086) as a part of a collaboration likewise initiated by a NIST ATP Project.

Woolley's team integrated a silicon sandwiched PCR type of reactor fabricated by Northrup and coworkers at LLNL with a glass CE chip fabricated at UC Berkeley. The Si reactor was mated to a side channel through a polypropylene sleeve. An HEC sieving matrix was used as an electrophoretic valve to separate the PCR solutions from the CE channels.

Much later, Ramsey and coworkers simply placed the PCR mix in a plastic reservoir on the chip and thermally cycled the entire chip on a conventional cycler. This was followed by injection as done earlier. This cycler was much slower than the hybrid device developed in the Berkeley-LLNL collaboration but did lead to ostensibly successful amplifications (Waters, L. C., Jacobson, S. C., Kroutchinina, N., Khandurina, J., Foote, R. S. and Ramsey, J. M., 1998, 70 (1) *Anal. Chem.* 158–162).

By way of further background, attention is likewise called to the following U.S. Pat. Nos: 20 4,821,997; 5,241,363; 5,554,276; 5, 585,069; 5,593,838; 5,603,351; 5,632,876; 5,643,738; and, 5,681,484.

It is respectfully submitted that each of the cited references merely defines the state of the art, or highlights aspects of the problems addressed and ameliorated according to the teachings of the present invention. The same are also fully referenced, and upon review each is clearly distinguished, as will be seen from the IDS filed concurrently herewith. Accordingly, further discussions of these references has been omitted at this time due to the fact that each of the same is readily distinguishable from the instant teachings to one having a modicum of skill in the art, as shall be denoued by the claims which are appended hereto.

To date the present inventors are not aware of any successful efforts to fabricate a fully integrated monolithic small volume PCR-CE device in glass using thin film metal heaters and thermocouples to thermally cycle sub-microlitre PCR volumes. Accordingly it is the longstanding need to address and ameliorate this concern which is a primary focus of the teachings of the present invention.

OBJECTS AND SUMMARY OF THE INVENTION

A submicroliter PCR type of a reaction chamber is taught for the amplification of specific diagnostic targets using PCR, among other things. Subject amplicons are then directly injected into microfabricated CE channels for fragment size analysis, or use with related biomolecular assays.

According to a preferred embodiment, PCR chambers and CE channels are etched into a thickened glass substrate using chemical etching. A thin (for example 0.20 mm) glass substrate is bonded to the etched surface defining the chambers and channels. The thin substrate utilizes a thermocouple or platinum resistance temperature sensing device on its interior or exterior surface in combination with a platinum or Peltier heater on the external surface for driving thermal cycling.

Briefly stated, a fully integrated monolithic small volume PCR-CE device in glass, or the like materials, is fabricated using thin film metal heaters and thermocouples to thermally cycle sub-microliter PCR volumes. Successful amplification of a PCR fragment is demonstrated on a PCR-CE chip. The process utilizes a linear polyacrylamide surface coating coupled with addition of BSA to the amplification buffer to obtain amplification efficiencies comparable to a positive control. The micro-reactor reduces significantly the time required for amplification and the reaction volume within the context of a sub-microlitre regime.

Likewise addressed are the known problems connected with reliable microfabrication of metal coatings and the insulating layers required to shield these layers from the PCR reaction itself, and the longstanding unresolved issue of exposed metal regions in the PCR-CE chip resulting in electrolysis of water and bubble formation whenever a voltage is applied. The instant teachings employ external heaters and thermocouples and, as such, have alleviated many of these problems. Heaters and thermocouples may still be thin film deposited after chip bonding allowing for easy scale-up to multichannel devices. In addition, direct deposition of these chip components insures good thermal contact with, for example, a PCR reactor.

According to a feature of the invention there is provided in a fully integrated glassine monolithic small volume PCR-CE device, the improvement which comprises; thin metal heating means, and thermocoupling means for cycling sub-microliter PCR volumes.

According to a further feature of the invention there is provided a method for microfabrication of an integrated PCR-type of device by positioning a series of chambers, including a microcapillary electrophoresis system which further comprises a multiplicity of fluidly communicant microtubules, on a chip-based substrate, the improvement comprising; providing a means for delivering fluid samples to the chambers as well as a means for removing the samples from the chambers, disposing resistive heating means on the chip-based substrate by thin film deposition, and harmonizing thermal cycling and resistance temperature sensing and concomitant adjustments by means of utilizing cycling control software further comprising heating and cooling times as part of a user-set hold time such that the hold time at each temperature does not begin until the actual temperature is within a user-defined percentage of a predetermined set point.

According to yet another feature of the invention there is provided a microfabricated reaction chamber system, comprising, in combination; a substrate member having at least a plurality of cavities disposed thereon; a means for driving thermal cycling; a supplemental means for resistance temperature sensing, an electrical means for connecting with a power source for applying a desired voltage, at least a software means for integrating said means for driving thermal cycling, said supplemental means for resistance temperature sensing, and said electrical means for connecting whereby a desired power level flowing through said electrical means for connecting and a desired temperature level is maintained with respect to a range defined by the difference in temperature of said at least one cavity and said supplemental means for resistance temperature sensing.

BRIEF DESCRIPTION OF THE DRAWINGS

The above-mentioned and other features of this invention and the manner of obtaining them will become more apparent, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
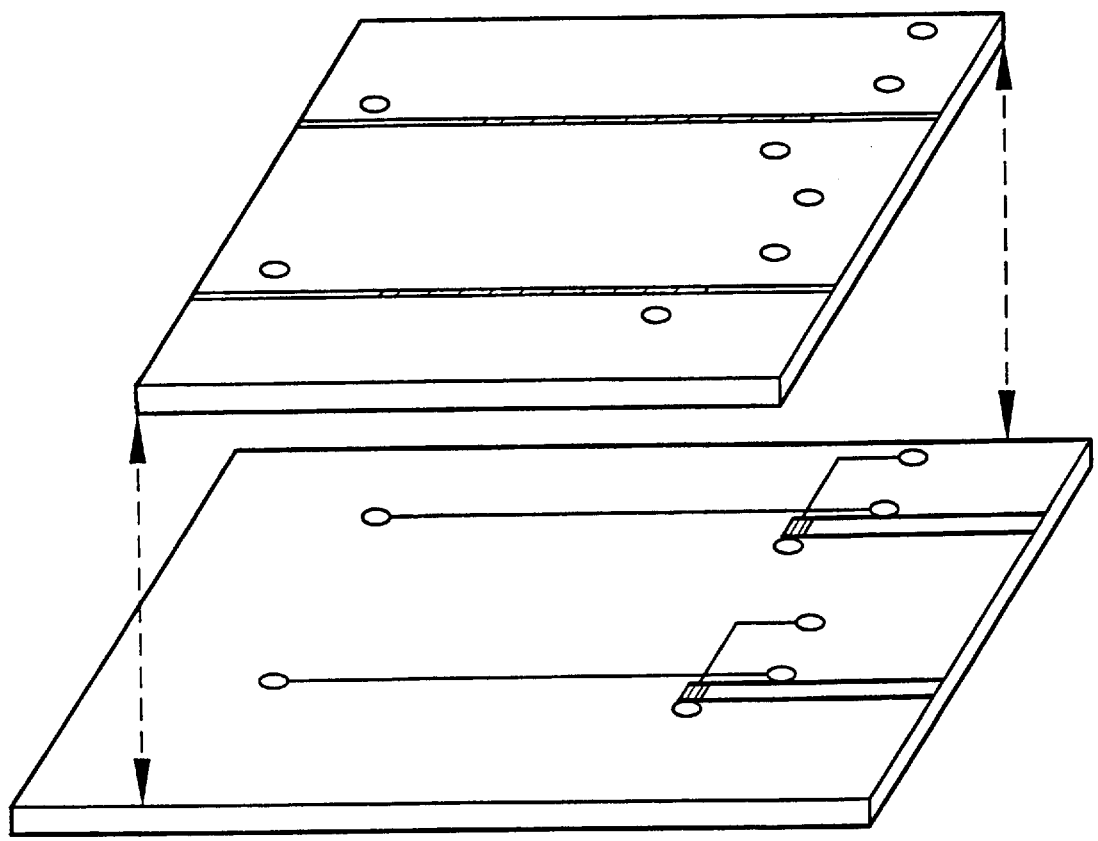
FIG. 1 is a prior art example of a generic design for a chip-based reaction chamber assembly.

The present inventors, realizing that one of the most desirable features of microfabricated analysis systems is the ability to integrate multiple reaction processes onto a single monolithic substrate (Woolley, A. T. and Mathies, R. A., 1994, 91 *PNAS* 11348–11352; Simpson. P. C., Woolley, A. T. and Mathies, R. A., 1998 95 *Proc. Natl. Acad. Sci. USA*. 2256–2261) have developed the teachings of the present invention. In this way the benefits of miniaturization are imparted to all steps in an assay, and the often time consuming and error prone manual transfer of samples between the various steps can be eliminated.

Miniature reaction chambers are needed for carrying out a variety of chemical reactions in fluid samples. In particular, the present invention provides devices incorporating miniature reaction chambers wherein the temperature of the chamber can be monitored and controlled. Further, as miniaturized devices, the devices of the invention provide the benefits of low volume reactions (e.g, low sample and reagent volume requirements), high thermal transfer rates, flexibility of applications and integratability of additional functions, reproducible standardized mass production of the devices, ability to perform multiple simultaneous analyses/reactions in small spaces leading to greater automability, and a variety of other advantages.

By "low volume" it is meant the reaction chambers of the present invention will typically have a volume of from about 0.001 $\mu$l to about 10 $\mu$l. Preferably, the devices of the present invention will have a volume of from about 0.01 $\mu$l to about 1 $\mu$l and more preferably, about 0.02 $\mu$l to about 0.5 $\mu$l.

The reaction chambers and devices of the present invention have a wide variety of uses in chemical and biotechnology applications where controllable and monitorable temperatures are desirable, such as nucleic acid manipulation, e.g., amplification by PCR, extension by polymerase, thermal cycling, labeling reactions, sizing and hybridization and fragmentation reactions. In particularly preferred embodiments, the reaction chambers and devices herein described, can be used for PCR amplification, which is extremely temperature dependent. PCR amplification generally involves the use of one strand of the target nucleic acid sequence as a template for producing a large number of complements to that sequence.

Generally, two primer sequences complementary to different ends of a segment of the complementary strands of the target sequence hybridize with their respective strands of the target sequence, and in the presence of polymerase enzymes and nucleoside triphosphates, the primers are extended along the target sequence. The extensions are melted from the target sequence and the process is repeated, this time with the additional copies of the target sequence synthesized in the preceding steps. PCR amplification typically involves repeated cycles of denaturation, hybridization and extension reactions to produce sufficient amounts of the target nucleic acid. The first step of each cycle of the PCR involves the denaturation of the nucleic acid duplex formed by the primer extension.

Once the strands are denatured, the next step in PCR involves hybridizing the denatural strands with primers that flank the target sequence. The primers are then extended to form complementary copies of the target strands. For successful PCR amplification, the primers are designed so that the position at which each primer hybridizes along a duplex sequence is such that an extension product synthesized from one primer, when denatured from the template (complement), serves as a template for the extension of the other primer. The cycle of denaturation, hybridization, and extension is repeated as many times as necessary to obtain the desired amount of amplified nucleic acid.

Typically, strand separation is achieved by heating the reaction to a sufficiently high temperature for a sufficient time to cause the denaturation of the duplex but not to cause an irreversible denaturation of the polymerase enzyme (For example, see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art.

Template-dependent extension of primers in PCR is catalyzed by a polymerizing agent in the presence of adequate amounts of four deoxyribonucleotide triphosphates (typically dATP, dGTP, dCTP, and dTT) in a reaction medium which comprises the appropriate salts, metal cations, and pH buffering system. Reaction components and conditions are likewise well known in the art. Suitable polymerizing agents are enzymes known to catalyze template-dependent DNA synthesis.

The reaction chambers of the present invention are particularly suited for use as a micro-PCR devices. In particular, the precise temperature monitoring and control within the reaction chamber allows the use of these chambers in the complex thermal cycling programs used in PCR based operations. Accordingly, in a specific aspect, the reaction chambers described herein may incorporate effective amounts of the reagents used in PCR reactions, as described above. By effective amount is meant that the reagents are provided within the reaction chamber in sufficient quantity and concentration, i.e., non-limiting amounts, so that amplification of a target nucleic acid may be carried out. Such amounts can be readily determined by those of ordinary skill in the art and may be extrapolated from readily available sources in the literature without undue experimentation.

The reaction chambers and/or devices of the present invention can be designed and reproducibly fabricated in large quantities from a solid substrate material using a variety of known methods and materials. For example, injection molding techniques may be used to fabricate all or a portion of the reaction chamber. Materials suitable for injection moldings include a variety of plastics and other polymers, e.g., polystyrene, polypropylene, etc. Generally, the material from which the reaction chambers and devices are to be fabricated will be selected so as to provide maximum resistance to the full range of conditions to which the device will be exposed, e.g., extremes of temperature, salt, pH, application of electric fields, e.g., in electrophoretic analysis embodiments, as well as compatibility with reagents and other materials used in fabricating the devices. The teachings of the present invention likewise contemplate, and have incorporated the use of photoresistive plastics.

In preferred embodiments, the devices of the invention which incorporate the miniature reaction chambers herein described are made using microfabrication techniques generally used in the semiconductor and microelectronics industries. These techniques include film deposition processes such as spin coating, electrodeposition, low-pressure vapor deposition, laser fabrication processes, photolithographic methods such as UV or X-ray processes, or etching processes which may be performed by either wet chemical processes or plasma processes.

Where these microfabrication methods are used, it will generally be desirable to fabricate the reaction chamber of the invention from materials similar to those used in the semiconductor industry, i.e., silica, silicon, photoresists, plastics or gallium arsenide substrates. For example, U.S. Pat. No. 5,252,294, to Kroy, et al., incorporated herein by reference in its entirety for all purposes, reports the microfabrication of a silicon based multiwell apparatus for sample handling in biotechnology applications using the above described methods.

Methods of etching substrates are well known in the art. For example, the first sheet of a substrate, e.g., silica, may be overlaid with a photoresist. A photolithographic mask may expose the photoresist in a pattern which reflects the pattern of wells to be etched on the surface of the sheet. After removing the exposed photoresist, the exposed substrate may be etched to produce the desired wells and the like. Generally preferred photoresists include those used extensively in the semiconductor industry. Such materials include polymethyl methacrylate (PMMA) and its derivatives, and electron beam resists such as poly (olefin sulfones) and the like.

The miniature reaction chambers and devices of the present invention are generally characterized by their relatively small size and ability to be used for extremely small volumes of reactants. As discussed further below, it has been discovered that non-square reaction chambers are preferred to avoid the formation of air pockets within the chamber itself. For example, round or elliptical reaction chambers having the above-described volumes are preferred according to the teachings of the present invention.

According to the instant teachings, the reaction chambers described herein are fluidly connected to one or more analytical devices or chambers, and comprise a preparative step for the particular analysis to be performed. For example, the reaction chamber may be fluidly connected to a chamber which includes an oligonucleotide array as one surface of this latter chamber. The chamber may have been used for preparation fragmentation, amplification or labeling of nucleic acid fragments in a sample, prior to introduction to the oligonucleotide array.

Oligonucleotide arrays generally include a substrate having a large number of positionally distinct oligonucleotide probes attached to the substrate. These oligonucleotide arrays, also described as "Genechips™," have been generally described in the art, for example, U.S. Pat. No. 5,143,854 and PCT patent publication Nos. WO 90/15070 and 92/10092. These arrays may generally be produced using chemical synthesis methods or light directed synthesis methods which incorporate a combination of photolithographic methods and solid-phase oligonucleotide synthesis methods. See Fodor et al., *Science*, 251:767–777 (1991), Pirrung et al., U.S. Pat. No. 5,143,854 (see also PCT Application No. WO 90/15070) and Fodor et al., PCT Publication No. WO 92/10092, all incorporated herein by reference.

These references disclose methods of forming vast arrays of peptides, oligonucleotides and other polymer sequences using, for example, light-directed synthesis techniques. Techniques for the synthesis of these arrays using mechanical synthesis strategies are described in, e.g., U.S. Pat. No. 5,384,261, incorporated herein by reference in its entirety for all purposes. Oligonucleotide arrays may generally be used to identify a particular mutation, or the presence of nucleic acids from an infectious agent, such as a virus or bacteria.

In another aspect, the reaction chamber described herein may be fluidly connected to a microcapillary electrophoresis device or array, for carrying out a size based electrophoresis of a sample. Microcapillary array electrophoresis generally involves the use of a thin capillary which may or may not be filled with a particular separation medium. Electrophoresis of a sample through the capillary provides a size based separation profile for the sample.

The use of microcapillary electrophoresis in size separation of nucleic acids has been reported in, e.g., Woolley and Mathies, *Proc. Nat'l Acad Sci. USA* (1994) 91:11348–11352, incorporated herein by reference in its entirety for all purposes. Microcapillary array electrophoresis generally provides a rapid method for size based sequencing, PCR product analysis and restriction fragment sizing. The high surface to volume ratio of these capillaries allows for the application of higher electric fields across the capillary without substantial heating, consequently allowing for more rapid separations. Furthermore, when combined with confocal imaging methods, these methods provide sensitivity in the range of attomoles, which is comparable to the sensitivity of radioactive sequencing methods.

Microfabrication of capillary electrophoretic devices has been discussed in e.g., Jacobsen, et al., *Anal. Chem.* (1994) 66:1114–1118, Effenhauser, et al., *Anal. Chem.* (1994) 66:2949–2953, Harrison, et al. *Science* (1993) 261:895–897, Effenhauser, et al. *Anal. Chem.* (1993) 65:2637–2642, and Manz, et al., *J. Chromatog.* (1992) 593:253–258. Typically, these methods comprise photolithographic etching of micron scale capillaries in a silica or other crystalline substrate or chip.

In many capillary electrophoresis methods, silica capillaries are filled with an appropriate separation medium. Typically, a variety of separation media known in the art may be used in the microcapillary arrays. Examples of such media include, e.g., hydroxyethyl cellulose, polyacrylamide and the like. Generally, the specific gel matrix, running buffers and running conditions are selected to maximize the separation characteristics of the particular application, e.g., the size of the nucleic acid fragments, the required resolution, and the presence of native or denatured nucleic acid molecules.

In addition to its use in nucleic acid "fingerprinting" and other sized based analyses, the capillary arrays may be used in sequencing applications. In particular, gel-based sequencing techniques may be readily adapted for capillary array electrophoresis. For example, capillary electrophoresis may be combined with the Sanger dideoxy chain termination sequencing methods, which would be known to those skilled in the art. (See also Brenner, et al., *Proc. Nat'l Acad. Sci.* (1989) 86:8902–8906). In these methods, the sample nucleic acid is amplified in the presence of fluorescent dideoxy nucleotide triphosphates in an extension reaction. The random incorporation of the dideoxy nucleotides terminates transcription of the nucleic acid. This results in a range of transcription products differing from another member by a single base. Size based separation then allows the sequence of the nucleic acid to be determined.

Figure 9A:
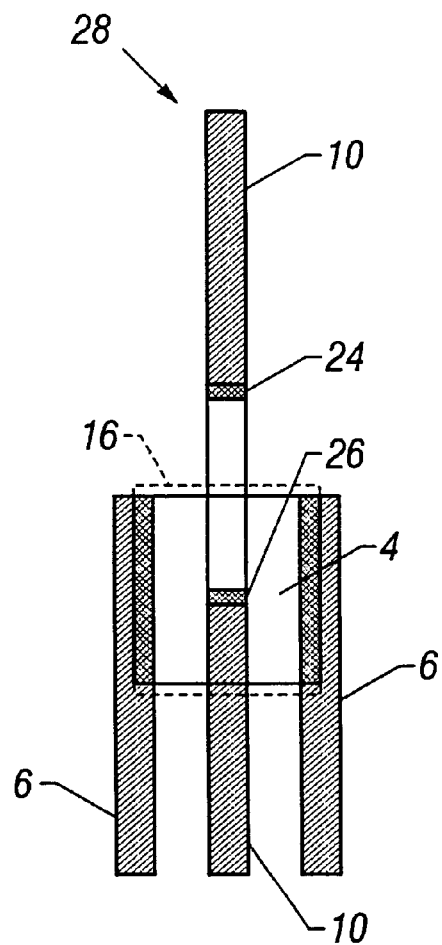
FIG. 9A is an illustration of an embodiment of a microvolume microcapillary electrophoresis device of the invention, in which a top view of the reaction chamber of the device is shown.
Figure 9B:
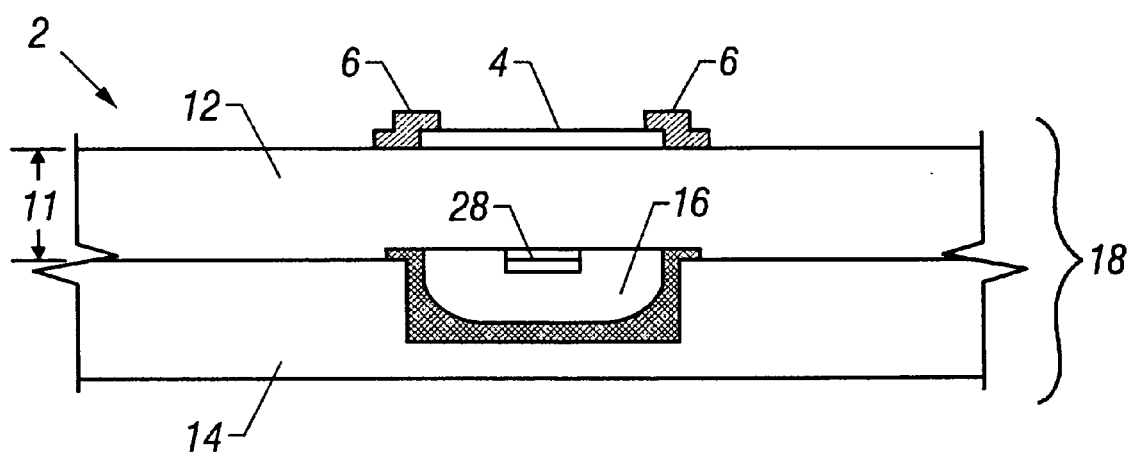
FIG. 9B is a side view of the reaction chamber shown in FIG. 9A.
Figure 10A:
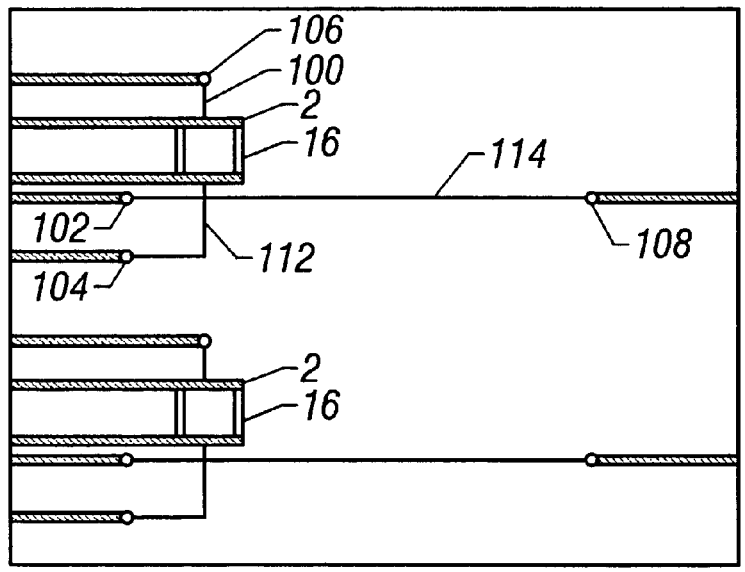
FIG. 10A is an illustration of a reaction chamber of the invention integrated into a capillary electrophoresis device, showing the layout of a bottom planar member with microcapillary channels and reaction chamber wells etched into its surface.
Figure 10B:
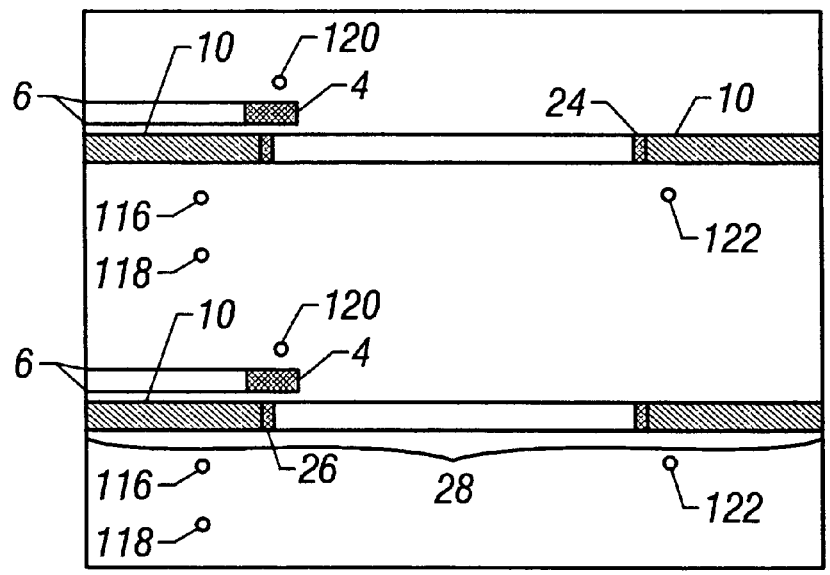
FIG. 10B is an illustration of a top planar member on which is deposited a thermocouple and a resistive heater.
Figure 10C:
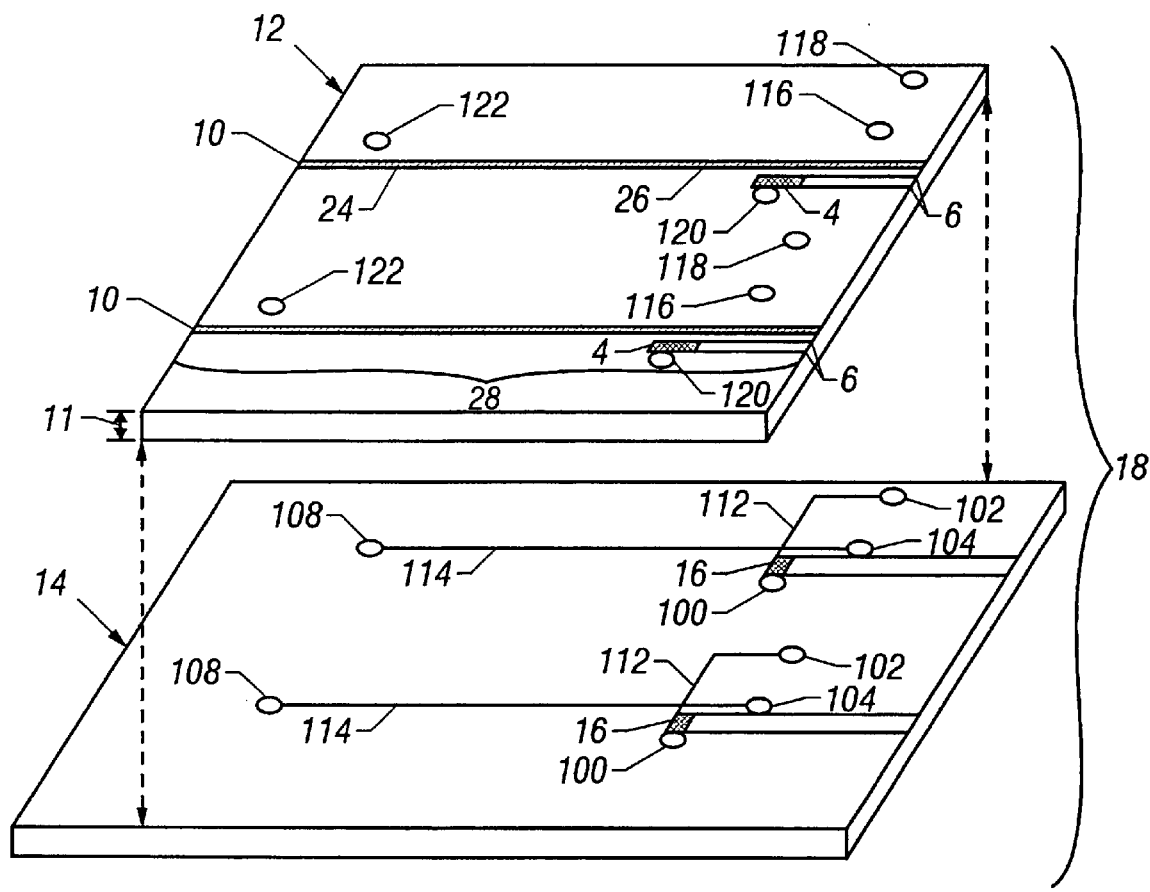
FIG. 10C is a perspective view of the mating of the top and bottom planar members shown in FIGS. 10A and 10B.

Referring now to FIG. 1, prior art example of a reaction for use with respect to a microcapillary electrophoresis device is shown. (See also Brenner, et al., *Proc. Nat'l Acad. Sci.* (1989) 86:8902–8906). Artisans will readily perceive the required layout of the capillary channels, (FIGS. 10A and 10C, 100, 112, 114) reaction chamber (FIGS. 9A and 9B, 16) and deposited electrical leads (FIGS. 9A and 9B, 6) on a planar member (FIGS. 9B and 10A, 14). Likewise, those skilled in the art will readily understand how the orientation whereby a second illustrated planar member (FIGS. 9B and 10B, 12) mates with the first. FIG. 1 generally shows an overlaying of two planar members which form the overall body (FIGS. 9B and 10C, 18) of the device which incorporates the reaction chamber connected to a microcapillary array.

In addition to including one or more of the above described elements, the reaction chambers of the present invention include one or more additional elements which aid in the particular reaction/analytical operation of the reaction chamber, including, e.g., mixers, pumps, valves, vents and the like.

Often, the convective forces resulting from the heating of a fluid sample within a reaction chamber will be sufficient to adequately mix that sample. However, in some cases it may be desirable to provide additional mixing elements. A variety of methods and devices may be employed for mixing the contents of a particular reaction chamber. For example, mixing may be carried out by applying external agitation to the reaction chamber. Typically, however, the reaction chambers of the present invention have incorporated therein, devices for mixing the contents of the reaction vessel.

Examples of particularly suitable mixing methods include electrophoretic mixing, wherein the application of an electric field across the sample results in a movement of charged components within the sample and thus the mixing of the sample. Alternative suitable mixers include lamb-wave transducers which may be incorporated into the reaction chambers. See, Published PCT Application No. WO 94/05414.

The reaction chambers described herein will also typically include a means for delivering a fluid sample to the reaction chamber as well as a means for removing the sample from the chamber. This may include a simple sample introduction and removal port whereby the sample is manually introduced and/or removed from the reaction chamber, as described above. However, as the reaction chambers of the invention are typically integrated within devices which include additional reaction/analysis chambers, it will typically be desirable to include one or more micropumps for transporting a fluid sample from one chamber to another.

A number of positive displacement micropumps have been described for micron/submicron scale fluid transport including lamb-wave devices, see for example, U.S. Pat. No. 5,006,749, electrokinetic pumps, diaphragm pumps, applied pressure differentials and the like. In particularly preferred embodiments, applied pressure differentials are used to affect fluid transport within the device, i.e., between two or more reaction chambers. In particular, the device may be provided with a pressure or vacuum manifold which can be used to selectively apply a pressure differential between two reaction chambers, forcing a sample to move from a high pressure chamber to a low pressure chamber.

Selective application of the pressure differentials can be carried out manually, i.e., applying a vacuum or pressure to a particular reaction chamber through an opening in the chamber, or it may be carried out using a pressure manifold employing valves as described herein, which valves may be selectively operated to direct pressure or vacuum to a given reaction chamber upon demand, or according to a programmed protocol.

As referenced above, valve structures can also typically be included in devices which incorporate the reaction chambers herein described. Typically, these valves will include, e.g., a deflectable diaphragm which when in a non-deflected position, rests against a valve seat blocking fluid flow between, e.g., a reaction chamber and a fluid channel. Deflection of the diaphragm thus allows fluid flow between the reaction chamber and fluid channel.

For a number of applications, it may be desirable to include a vent within a given reaction chamber. Typically, this will be the case where reaction conditions result in the evolution or expansion of gas or fluid within the chamber. Such events will typically be fitted with a poorly wetting filter plug to allow for the passage of gas, while retaining liquid.

Figure 2A:
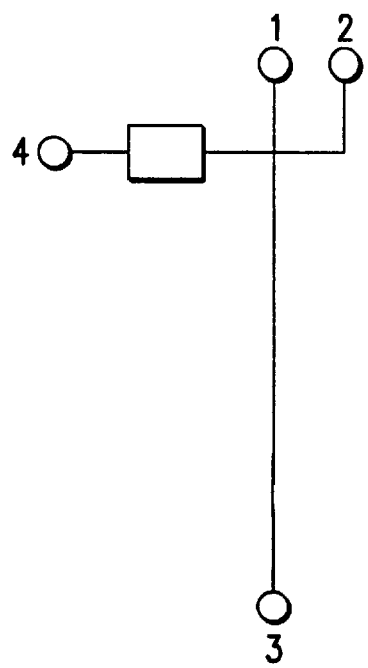
FIG. 2 is a series of schematic illustrations showing the evolution of two preferred embodiments of chip designs according to the teachings of the present invention.

Control of reaction parameters within the reaction chamber may be carried out manually, but is preferably controlled via an appropriately programmed computer. In particular, the EMF from the thermocouple and the input for the power source will typically be interfaced to a computer which is programmed to receive and record data via an analog-digital/digital-analog (AD/DA) converter. The same computer will typically include programming for instructing the delivery of appropriate current to allow the reaction chamber to follow any number of predetermined time/temperature profiles, e.g., thermal cycling for PCR, and the like. Referring now to FIG. 2, the evolution of some of the objects of the present invention is set forth. Namely, it is noted that initially, a square reactor design was investigated (FIG. 2*a*.), and improved upon. Reservoirs, wells or indentations 1, 2, 3 (FIGS. 10A and 10C, 102, 104, 106, and 108) and were each utilized for the cycling according to the instant teachings, and are extensions of apertures (FIGS. 10B and 10C, 116, 118, 120, and 122) extending through a top portion of the substrate-means (chip) as shown in prior art FIG. 1.

Figure 2B:
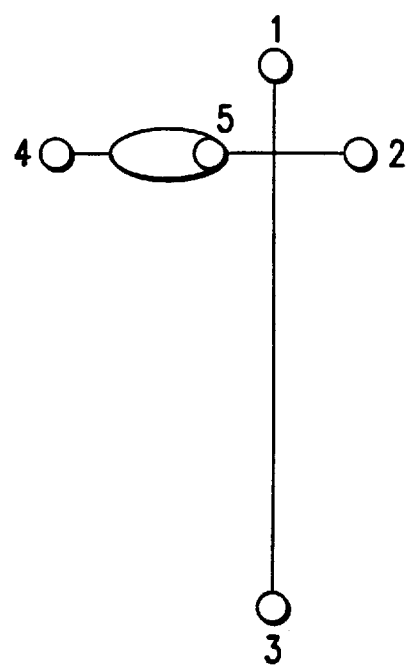

At an etch depth of 8 $\mu$m the volume of the reactor was approximately 1 $\mu$L. Previously, it had been noted that while filling the chamber, air became trapped in the reactor corners. During thermal cycling, expansion or the trapped air forced liquid out of the reaction chamber. To overcome this problem the reactor was redesigned as an ellipse (FIG. 2*b*). The elliptical design reduced slightly the reactor volume (0.3 $\mu$L) but allowed bubble free filling of the chip. In addition, an extra hole (numbered 5 in FIG. 2*b*) was drilled close to the reaction T to allow independent filling of the reaction chamber.

Thus, inject and separation channels could be filled with the HEC separation buffer while the PCR reactor contained only the amplification mixture. The majority of the work according to preferred embodiments of the present invention utilizes elliptical reactor patterns, etched to a depth of from about 13—to about 22 $\mu$m. Deep channels permit easy replacement of the viscous sieving matrix. Likewise, it was discovered that most preferred embodiments were those have outside heaters and using platinum films with an etch depth of about 20 $\mu$m.

By way of further general background to the instant teaching, planar members are also referred to herein as "substrates," "slides" or "chips." These planar members may be made from a variety of materials, including, e.g., plastics (compression molded, injection molded, machined, etc.), glass, silicon, quartz, or other silica based materials, gallium arsenide, and the like. Preferably, at least one of the planar members is glass. The cavity or well that forms the basis of the reaction chamber is generally disposed within the first planar member, or may be a combination of an aperture in the first and a well region or indentation in the second. This cavity may be machined or etched into the surface of the first planar member, or alternative, may be prepared in the manufacturing of the first planar member, such as where the planar member is a molded part, e.g., plastic.

Referring now once again to FIG. 2, Temperature control for the reaction chamber is provided by a resistive heater means 4 deposited within the reaction chamber. The resistive heater means is shown in FIG. 2 as a thin film resistive heater deposited on the bottom surface of the reaction well. Typically, the resistive heater means comprises a thin resistive metal film, coated with an insulating layer (not shown) to prevent electrolysis at the surface of the heater, and/or electrophoresis of the sample components during operation with fluid samples.

In preferred embodiments, the thin metal film is a thin chromium film ranging in thickness from about 200 Å. Deposition of the heater may be carried out by a variety of known methods, e.g., vacuum evaporation, controlled vapor deposition, sputtering, chemical decomposition methods, and the like. The protective layer over the heater may comprise a number of nonconductive materials, e.g., a TEFLON coating, $SiO_2$, $Si_3N_4$, and the like. In particularly preferred embodiments, the heater may be coated with a $SiO_2$ layer. The $SiO_2$ layer may generally be deposited over the heater film using methods well known in the art, e.g., sputtering. Typically, this $SiO_2$ film will be from about 1000 Å to about 4000 Å thick The resistive heater is connected to electrical leads which allow the application of a voltage across the heater, and subsequent heating of the reaction chamber. A variety of conducting materials may be used as the electrical leads, however, gold leads are preferred. In particularly preferred embodiments, the electrical leads comprise a gold/chromium bilayer, having a gold layer of from about 2000 Å to about 3000 Å and a chromium layer of from about 250 Å to about 350 Å. This bilayer structure is generally incorporated to enhance the adhesion of the gold layer to the surface of the substrate, with the chromium layer going down first in preferred embodiments.

The temperature sensor may also be selected from other well-known miniature temperature sensing devices, such as resistance thermometers which include material having an electrical resistance proportional to the temperature of the material, thermistors, IC temperature sensors, quartz thermometers and the like.

The reaction chambers described herein will typically be incorporated in devices which include additional elements for sample manipulation, transport and analysis. In particular, the reaction chambers described herein will typically have an opening which is adapted for receipt of a fluid sample. Typically, these openings will include sealable closures which prevent leakage of the sample introduced into the chamber during operation. Sealable openings may include e.g., a silicone septum, a sealable valve, one way check valves such as flap valves or duck-billed check valves, or the like. Similarly, the reaction chamber may be provided with a means for removing the sample following the particular reaction. This may be the same as the sample introduction means, or may include an additional sealable opening in the reaction chamber.

In addition to openings in the chamber for sample introduction and removal, the reaction chambers herein described may be fluidly connected to additional reaction chambers to carry out any number of additional reactions. For example, one reaction chamber may be used to carry out a fragmentation reaction. Following this fragmentation reaction, the sample may be transported to a second reaction chamber for, e.g., PCR amplification of desired fragments, hybridization of the fragments to an array. Similarly, a first reaction chamber may be adapted for performing extension reactions, whereupon their completion, the sample may be transported to a subsequent reaction chamber for analysis, i.e., sequencing by capillary electrophoresis.

According to a currently contemplated best mode of the design a further modified embodiment likewise facilitates ease of filling, in addition, allows injection of the sample from the "heart" of the reaction chamber (FIG. 2c), by adjusting the position of supplemental aperture 5 positionally reactive to the rear of the disclosed design.

Several different glass types and thickness have been evaluated for PCR-CE chip fabrication. Soda lime glass, etched to a depth of 8 μm, was used in early designs. The etched plate and cover plate thickness was 1.1 mm and devices were patterned and etched according to Woolley et al. To allow greater etch depth, D263 and borofloat glasses were used in later designs and etched according to Simpson et al. Cover plate thicknesses (FIG. 9B and FIG. 10C, 11) of these glasses were 200 and 300 μm, respectively. At 200 μm thickness, substrates were difficult to handle and, for multiple processing steps, breakage was common.

Holes were drilled in individual etched bottom plates using a ¾ mm diamond-tipped drill bit, using the etched pattern as a template. Substrates were bonded to a blank glass slide using a resin/beeswax mixture to provide support and prevent break-out during drilling. The resin/beeswax was removed by soaking the substrate in trichloroethylene for 1 hour and, if necessary, by brushing the substrate gently with a nylon brush.

In the case of D263 and soda lime glass, bonding was performed at 550° C. for 3 hours. For borofloat, the temperature was increased to 624° C. Re-bonding was frequently required, since internal metal or insulating layers caused variations in surface topography and poor bonding was observed in these regions.

In addition to glass, plastic was also investigated as a PCR-CE chip material. PCR reaction wells were formed by drilling an appropriately sized hole in polymethylmethacrylate (PMMA). PMMA plates were bonded together by heating at 135° C. for 1 hour and cooling slowly. The compatibility of PMMA with PCR is discussed later.

Resistive heaters were deposited on the PCR-CE chip by thin film deposition (~2000 Å) of a metal on either the internal or external surface of the PCR reaction chamber. Chrome or platinum/titanium metal films were used. Titanium (~200 Å) acts as an adhesion layer for platinum (~1500 Å) and the combination was found to adhere very well to glass. By comparison chrome adhesion was worse. Chrome layers were deposited by evaporation, while platinum/titanium were plasma sputtered. Both techniques yielded films of comparable quality. Evaporation of platinum/titanium films proved more difficult.

Chrome heaters suffered significantly from oxidation both during the bonding process and subsequently during repeated thermal cycling experiments. After bonding, a chrome heater had an approximate resistance of 20 Ω. This rose to above 100 Ω after several weeks of experimental usage. At high resistance heating becomes increasingly more difficult (V=IR, P=I$^2$R). Platinum/titanium heaters were not found to suffer from this problem.

Initial experiments were performed with heaters deposited on the internal, etched surface of the chip. This approach, however, was improved upon since currents required to heat the chip to 95° C. caused degradation in the heater side-wall coating and eventual loss in electrical continuity. The situation can be likened to a fuse-blowing mechanism, whereby the metal melts when the current exceeds a particular amperage. Many attempts were made to thicken the metal side-wall coatings, including angling the substrate relative to the source during chrome evaporation and continually rotating the substrate during plasma deposition of platinum/titanium.

As an alternative, heaters (FIGS. 9A and 9B, 10B and 10C, 4) were deposited on the external flat surface of the chip. Aside from overcoming problems with side-wall coatings, this solution had a number of other advantages. Firstly, since heaters were deposited after bonding, metal films were not subjected to high temperatures which resulted in oxidation. Secondly, heaters could be removed and redeposited on a bonded chip. Thirdly, since the heater was not in direct contact with the PCR reaction mixture, no insulating coating (such as SiO$_2$) was required to provide a PCR compatible surface.

On the downside, the 200 μm separation of the heat source from the reactor caused temperature lag. This however, proved only a minor problem because equilibration times were fast and the reactor temperature was still sensed directly by an internal thermocouple.

Platinum/titanium films had a resistance in the range of from about 2–5 Ω. It was necessary to impedance match the ac amplifier output with the heater resistance to prevent distortion of the wave form at higher voltage outputs. Electrical connection to heaters was made using a conductive cement which could be removed and reapplied at any time.

Temperature of the PCR reaction mixture was monitored during thermal cycling by a thin film chrome/gold thermocouple (FIGS. 9A, 9B, 10B and 10C, 28). Sensing junctions (FIGS. 9A, 10B, 10C, 26) and reference junctions (FIG. 9A, FIG. 10B and FIG. 10C, 24) of the thermocouple were formed by overlay of a 1500 Å chrome layer with a 1500 Å gold layer (FIG. 9A, FIG. 10B and FIG. 10C, 10). It was necessary to use 100 Å of chrome as an adhesion layer for the gold. During chip bonding at >500° C. these two layers would diffuse into one another to form an alloy producing a thermocouple with a response not predicted by consideration of the difference in the Seebek coefficient for each metal. Thus, the thermocouple on each chip required calibration prior to use, although in general the response was in the range 55,000° C./V.–65,000° C./V. The measured resistance of each thermocouple was around 100 Ω.

In common with heaters, thermocouple deposition on the etched surface of the chip suffered from poor side-wall coating and it was therefore necessary to deposit thermocouples on the flat surface of the 300 μm top plate, on the flip-side to the heaters. To gain electrical access to the thermocouples, two 1.4 mm holes were drilled in the etched bottom plate prior to bonding. After bonding, conductive cement was used to extend the connections to the chip edge, where flat bladed copper clips could be attached.

The oxidation of chrome regions of the thermocouple during the bonding resulted in approximately 25% of all thermocouples failing (R=∞Ω). Alternative combinations of metals (platinum/titanium and gold and platinum/titanium and silver) were investigated to overcome this problem, but in these cases the emf generated per ° C., was less than for chrome/gold and difficult to measure accurately.

Since metal surfaces were found to inhibit PCR amplification, an insulating layer was coated over the temperature sensing junction of the thermocouple. In addition, the thermocouple was electrically isolated from the solution, since application of an injection voltage across the reactor caused electrolysis of water and bubble formation. For D263 and sodalime glass, silicon dioxide was used as an insulating layer, while a borofloat coating was used if the chip was fabricated from borofloat. In both cases the film was plasma sputtered to a depth of ~2000 Å. Over gold regions of the thermocouple these coatings were poor, suffering from pinholes and crazing. Coatings over chrome regions, by comparison were considerably improved. A moderately good coating of SiO$_2$, or borofloat over the entire junction was achieved by applying a final capping chrome layer over gold coated regions of the thermocouple. This additional layer did not affect the performance of the thermocouple.

Despite its distance from the heated region of the chip (4–5 cm), the thermocouple reference junction experienced a small temperature rise during thermal cycling, especially at longer denaturation hold times. The maximum increase was around 1° C. per 10 cycles. The increase was compensated for by periodic adjustment of the reference set point in the PCR program. In general, however, the temperature rise was <1° C. over 30 cycles.

Each thermocouple was individually calibrated using a series of temperature indicating fluids supplied by Omega. A thin smear applied to the top surface of the chip dried almost instantly to a mark. Heating caused the mark to liquefy at a stated temperature. Accuracy of melting was ±1% and the time response was on the order of milliseconds. The temperature gradient across the chip was assumed linear and calculated by simultaneously monitoring the temperature on both sides of the chip during heating. Further confirmation of the temperature accuracy was obtained by monitoring the boiling point of ethanol and/or water.

Dependent on the chip design, a number of different procedures were used to fill PCR-CE chips with the HEC separation matrix and the PCR reaction mixture. The primary objective was to fill the reactor with PCR mix and the remainder of the chip with HEC. In this way the HEC acts as an electrophoretic valve, restricting amplification to the heated reactor region and preventing contamination of injection and separation channels with PCR mix.

To fill reaction chambers bubble free, it was necessary to first flush the chamber with ethanol to wet the reactor surfaces. Ethanol has no inhibitory effect on Taq polymerase activity at or the 10% level. For PCR-CE devices of the design shown in FIG. 2b, HEC was flushed from well 3 of the separation channel as far as well 5 of the PCR chamber, thus filling inject and separation channels with the sieving matrix. The PCR chamber was next flushed with ethanol from well 4, followed by PCR reaction mixture. Due to the viscosity of the HEC buffer and the resistance to flow in the inject channel, this procedure fills only the reactor and no reaction mix is observed to flow into the inject channel. HEC also prevents flow of PCR reaction mixture during thermal cycling.

Figure 3A:
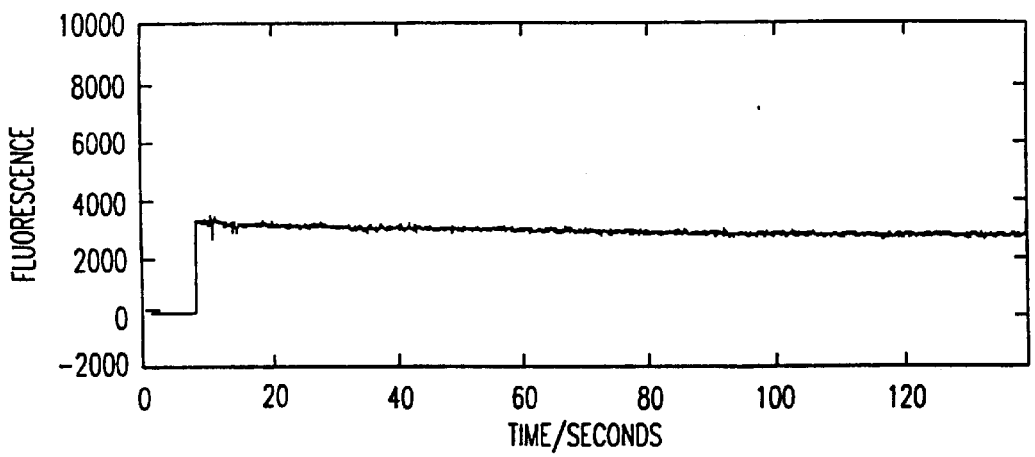
FIG. 3 is a series of three graphical representations plotting time (abscissa) against fluorescence (ordinate) in an analysis of an injection cross plug during a thermal cycling experiment according to teachings of the embodiments of the present invention.
Figure 3B:
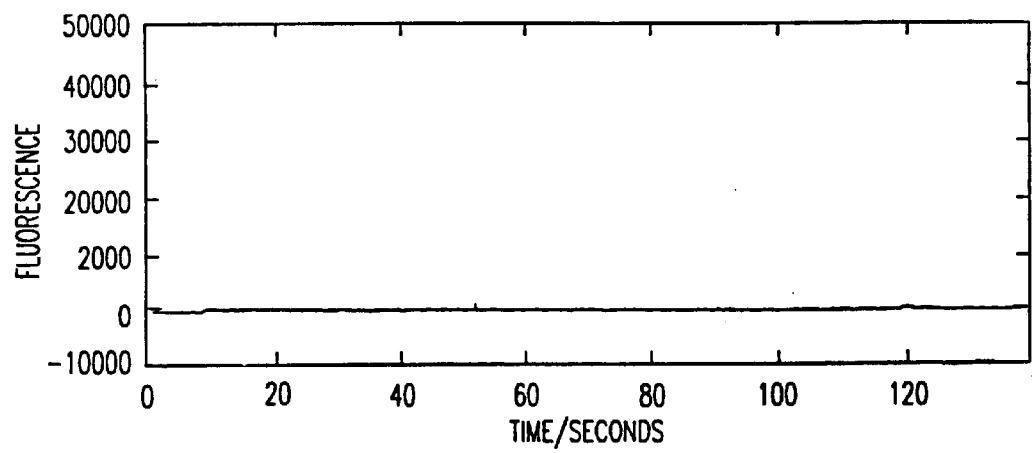
Figure 3C:
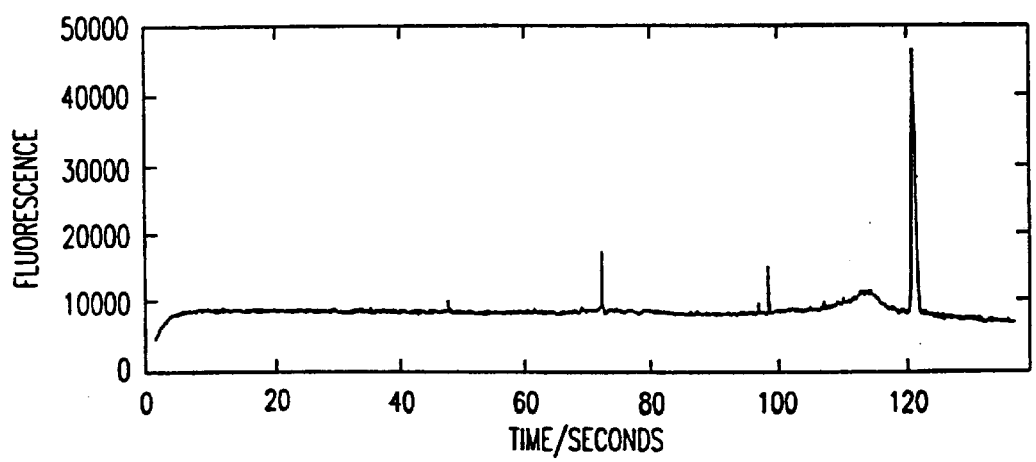

A PCR chip was filled with a solution of linearized pUC19 and electropherograms in FIG. 3 represent analysis of the injection cross plug before thermal cycling (a), after thermal cycling (b) and after thermal cycling following application of an injection voltage (c). Results show that the reaction mix remains confined to the reaction chamber during thermal cycling and is only transported to the injection cross after application of the appropriate voltages.

Figure 2C:
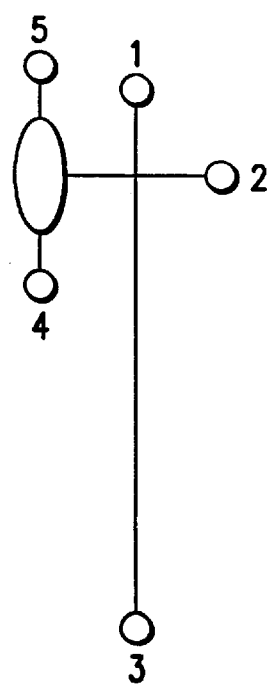

Devices of the design shown in FIG. 2c were filled in a different manner. Initially, HEC was flushed from reservoir 3 to a point just below the cross channel. Ethanol, followed by PCR reaction mix, was then flushed from reservoir 4, filling the reactor and injection region. A small air bubble was trapped between the amplification solution and the HEC. Next, HEC was flushed from reservoir 4 again until the air bubble migrated to reservoir 1. At this point the bubble was removed from the reservoir and replaced by fresh HEC. By monitoring movement of the bubble it was possible to ensure only the inject and separation channels were filled with HEC.

During thermal cycling, reactor wells were filled with mineral oil to prevent evaporation. In the absence of the oil, liquid evaporated from the wells at different rates causing siphoning. In addition, it was found that the lower surface tension of the mineral oil (and thus better wetting capabilities) prevented bubble formation. Ordinarily, rough drilled surfaces were poorly wet with the PCR amplification mixture and during thermal cycling trapped air would expand and force liquid out of the wells. This was prevented when wells were filled with mineral oil.

Figure 4A:
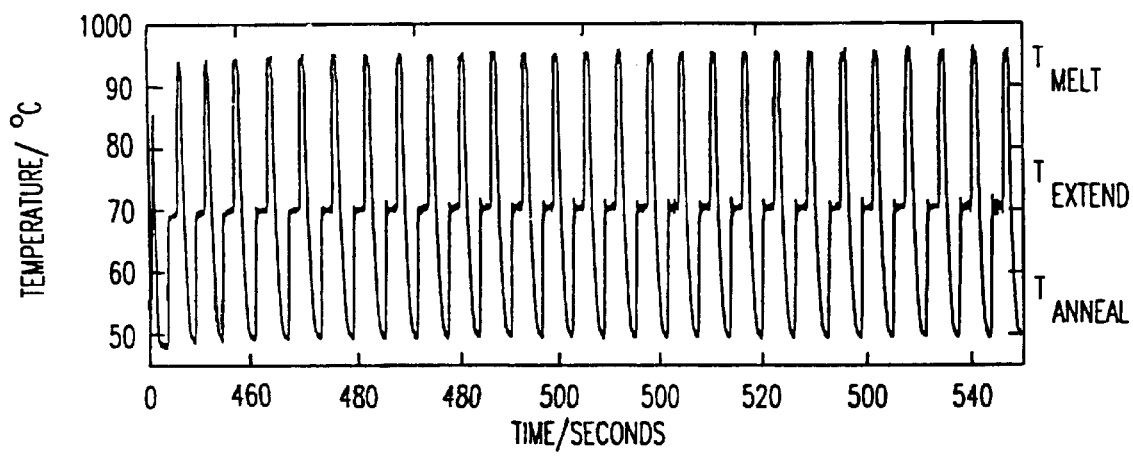
FIG. 4 is a graphical representation of temperature profile as a function of time during on-chip amplification of a 136 bp M13 fragment, and an expanded or detailed view of two cycles.
Figure 4B:
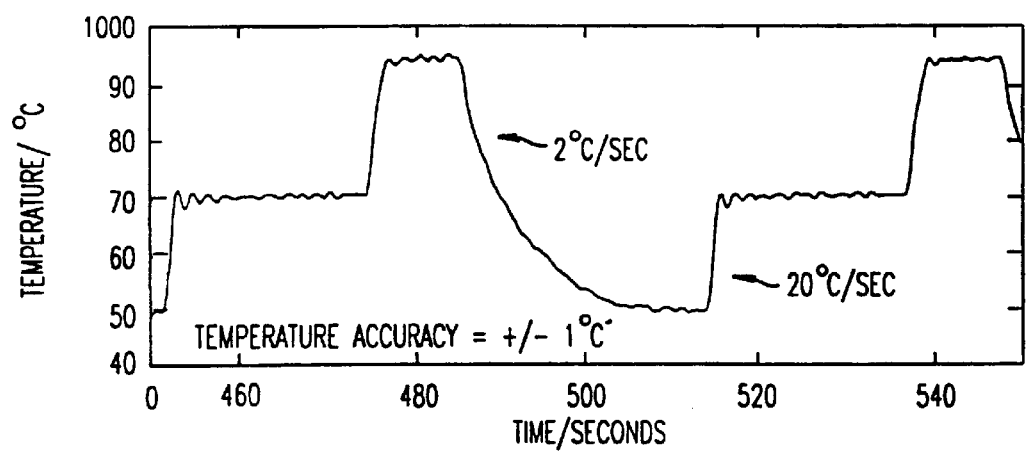

One major advantage of a microfabricated PCR device is the ability to do fast thermal cycling. A portion of a typical temperature profile recorded for a glass PCR-CE device is shown in FIG. 4. Heating rates in this case are 20° C./sec whilst passive cooling rates are 2° C./sec. Cooling rates may be significantly increased using forced air convection. The temperature of the reactor was controlled using proportional band control. Using this type of control the actual temperature never reaches the set temperature, always a slightly lower value. The temperature band in which the proportional control is active is set by the gain parameter (set in the software).

The higher the gain value the narrower the proportional band and the closer the actual temperature is to the set point. At lower gain values the proportional band is wider and the temperature difference between the actual and set temperatures is larger. Lower gain, values are advantageous for precise temperature control. For the majority of experiments a gain value of 20 was used. This gave a temperature offset of 3° C. at a set temperature of 95° C. Offsets were accounted for by means of a blank calibration cycle. The accuracy of temperature control at this gain value was ±1° C. determined at the denaturation temperature.

Early versions of the thermal cycling control software included heating and cooling times as part of the user-set hold time. This was problematic on the first PCR cycle as heating occurred from room temperature and the time taken to reach the set temperature was longer than for subsequent cycles. Recently, the program has been modified such that the hold time at each temperature does not begin until the actual temperature is within a user-defined percentage of the set point.

PCR amplification was performed using plasmids with M13 forward and reverse priming sites. Plasmids used were pBluescript SK+, pUC19 (with an insert) and M13mp18. The use of plasmids as templates is advantageous because of the high concentration of DNA available. For example, the Perkin-Elmer HIV-1 PCR kit is supplied with an HIV positive control at a concentration of $10^3$ copies per $\mu$L. By contrast dilution of plasmid targets permit starting concentrations of $10^6$ copies and higher. While reamplification of a reaction is possible to generate higher starting copy number. This was undesirable due to the formation of non-specific product. Table I shows starting template and amplicon size,

| Template | Amplicon size/bp |
|---|---|
| pBluescript SK+ | 260 |
| pUC19 (with insert) | 487 |
| M13mp18 | 136 |

Table 1: PCR product size versus starting template. Primers used for amplification were: 5'-CCCAG TCACG ACGTT GTAAA ACG-3' (forward primer) and 5'-AGCGG ATAAC AATTT CACAC AGG-3' (reverse primer). Standard cycling conditions on the PE480 were 95 (60 secs), 55 (60 secs), 72° C. (90 secs) for 30 cycles.

Figure 5A:
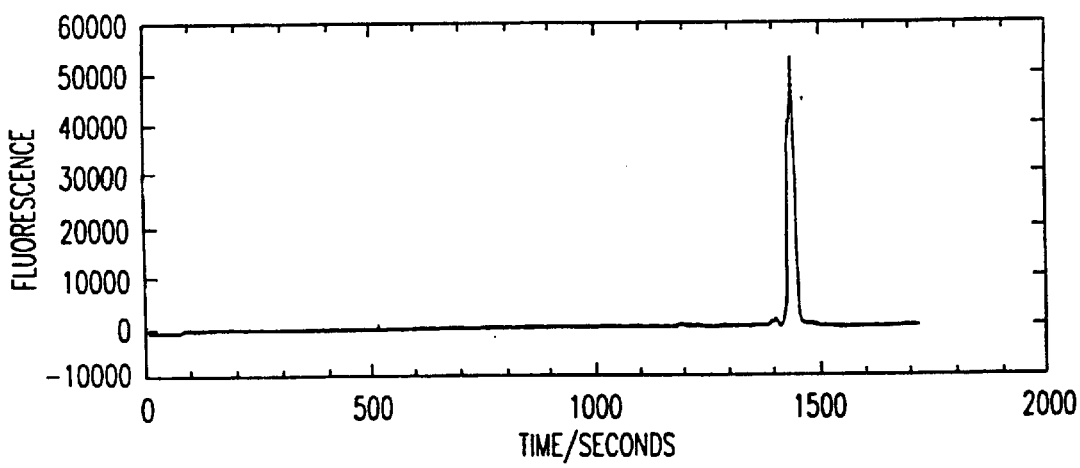
FIG. 5 is a series of electropherograms of plasmids amplified with M13 primers.
Figure 5B:
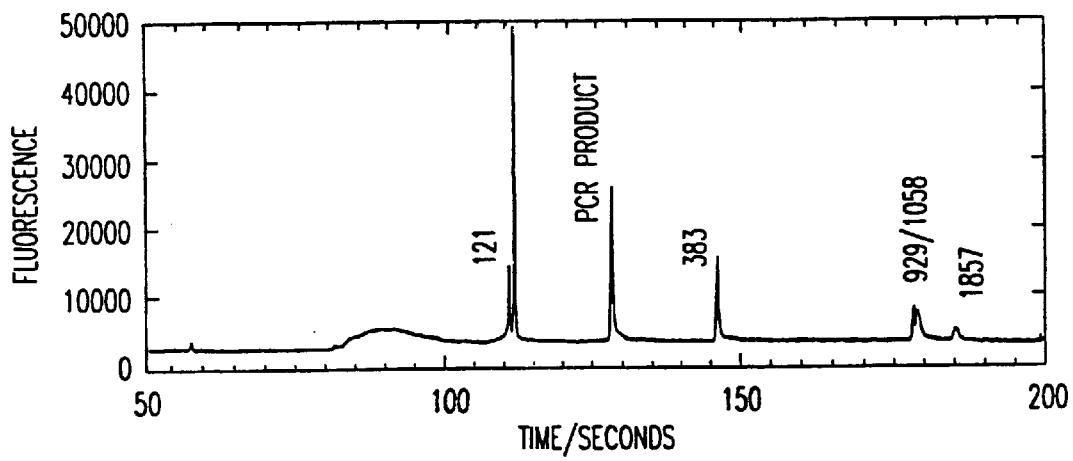
Figure 5C:
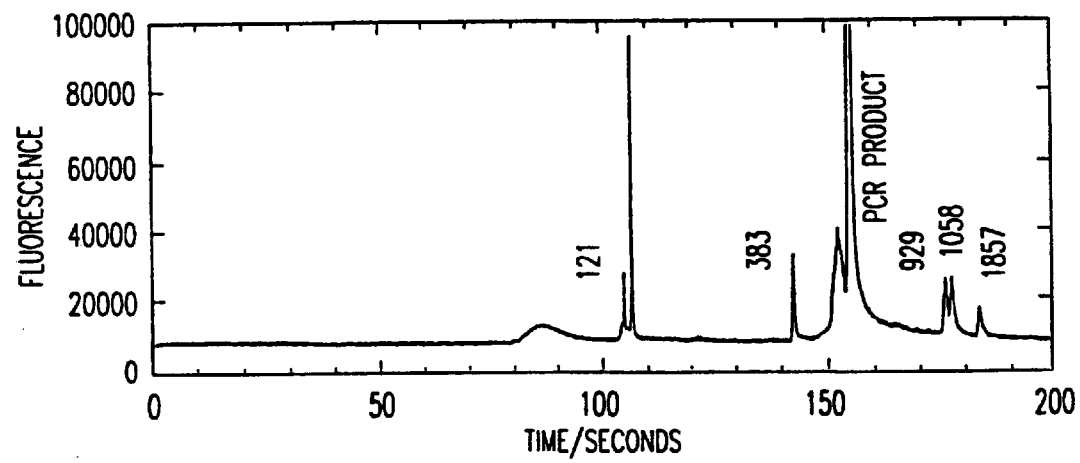

CE separations of the amplified products are shown in FIG. 5. Referring to the figure, capillary electrophoresis separation of M13mp 18 (sized independently against Phix 174 at 120 bp) are shown in FIG. 5a. FIG. 5b shows chip separation of pBluescript (260 bp) sized against pBr322-BBstN, while FIG. 5c is chip separation of pUC19 (with insert 487 bp) sized against PBr322-BstN1. Analysis of the M13 amplicon was performed on a capillary system, while pBluescript and pUC19 amplifications were analyzed in a microchannel.

The effect of the reactor surface on the efficiency of PCR amplification was studied. A series of HIV PCR mixtures were flowed through a chip reactor, containing an $SiO_2$ coated thermocouple, and then amplified under standard conditions in the PE480. Amplification efficiencies of the flow-through reactions were compared to positive control reactions (no chip contact) using agarose gel electrophoresis. To obtain equivalent amplification it was necessary to coat the surface of the glass reactor with linear polyacrylamide (LPA) and add bovine serum albumin (BSA) to the PCR buffer at concentration of 50 $\mu$g/mL (or higher). An LPA coated surface alone resulted in reduced amplification, while a naked glass surface (no coating) was found to completely inhibit the PCR reaction (no PCR band observed on a gel).

Absorption of Taq polymerase to the reactor walls was identified as a prime investigatory concern. A 0.5 $\mu$L spike of Taq into an unsuccessful amplification followed by reamplification yielded a positive result. However, it was not possible to simply increase the starting Taq concentration. Even at 4×Taq no band was observed after amplification of a reaction flowed through a naked reactor. Thus, all on-chip PCR reactions were carried out in an LPA coated reactor with 50 $\mu$g/mL of BSA added to the amplification buffer.

A PMMA surface was not found to significantly inhibit the PCR reaction at all. Amplification of a pBluescript target was carried out in PCR tubes coated with a thin layer of PMMA. Amplification efficiencies compared to a positive control reaction amplified in a polypropylene tube, were comparable. High resolution separations of ds DNA (271/281 bp of Phi X-174 almost baseline) were also possible in PMMA chips without coating of the channel walls.

The efficiency of amplification in glass PCR-CE chips was further evaluated by cycling PCR reactions in a chip containing no heater or thermocouple components. Temperature cycling was accomplished using the heating block of the PE480. Temperature was monitored using the internal thermocouple of the instrument and an externally chip-mounted copper-constantan thermocouple. Cycling temperatures were adjusted to compensate for temperature gradients across the chip. Amplified pUC 19 (with insert) reactions were flushed from the chip, collected into 5 μL of water and analyzed on a separate CE chip. Under standard cycling conditions (95° C. (60s), 55° C.(60s), 72° C.(90s); 30 cycles) no product peak was observed in the separation.

A reduction in the hold time at the denaturation temperature, however, yielded a successful amplification of the 487 bp fragment, with an amplification efficiency comparable to that of the positive control reaction (FIG. 5). Since chip PCR reaction volumes were sub-microlitre and thermal equilibration was fast, it is likely that 60 second hold times at 95° C. were sufficient to denature Taq polymerase early on in the reaction. Clearly reduced hold times at set cycling temperatures is desirable to speed chip amplification times. This data, however, demonstrates that it is also critical to preserve enzyme activity.

Figure 6A:
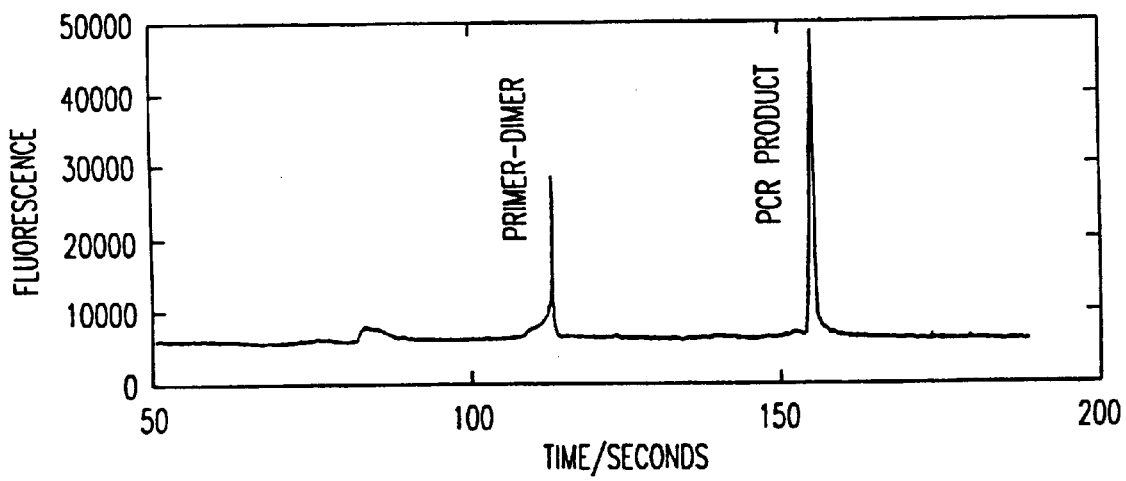
FIG. 6 shows on chip amplification of a 487 bp fragment with off-chip separation, the bottom view being a successful chip amplification and the top view a positive control.
Figure 6B:
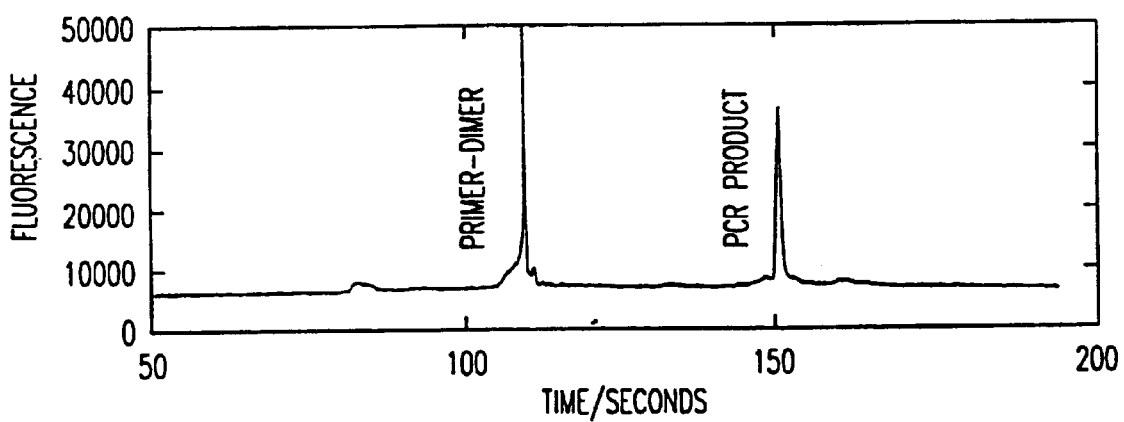
Figure 7:
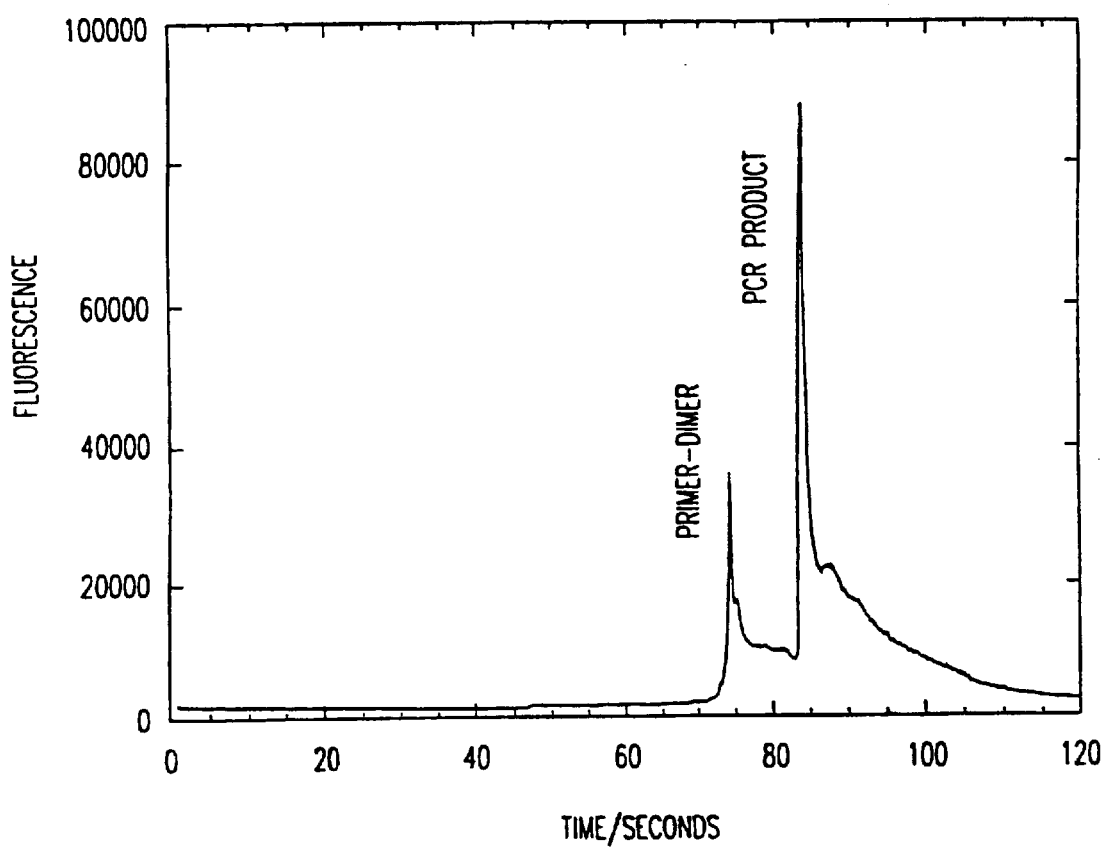
FIG. 7 graphically depicts on chip amplification of a 487 bp pUC19 vector plus insert; and, FIG. 8 shows a chip amplified reaction flushed from the reaction chamber with water, sandwiched between a positive and a negative control depiction.

Using the above experimental set-up, on-line amplification and separation of reaction products was performed. Prior to thermal cycling, the PCR reactor was filled with reaction mix and the injection and separation channels with a 0.75% HEC solution containing 0.2 μM thiazole orange. Access holes were again filled with mineral oil to prevent evaporation. After thermal cycling was complete, the mineral oil was removed and replaced with the separation buffer. FIG. 6 shows successful amplification of the PCR fragment.

A successful chip amplification of an M13mp18 target (on-chip heating and temperature control), with off-line capillary electrophoresis separation of the amplified product, was also demonstrated.

Figure 8A:
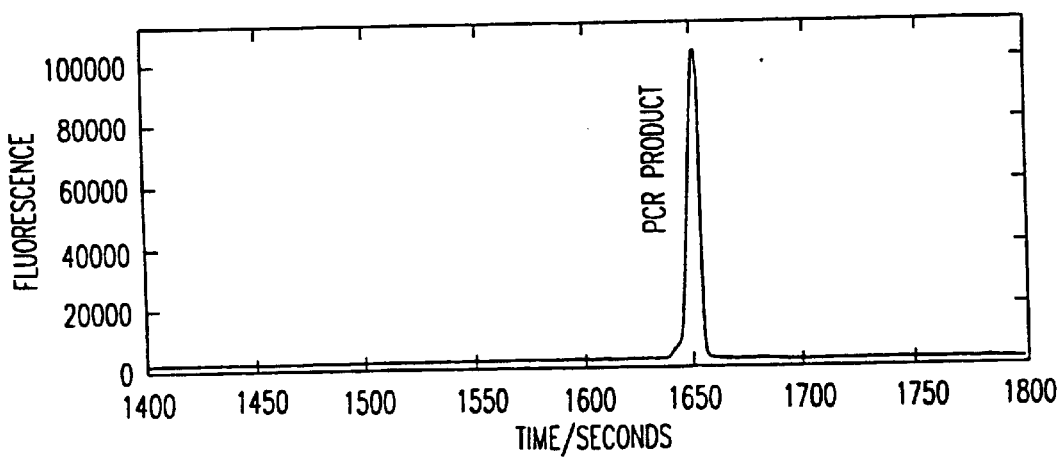
Figure 8B:
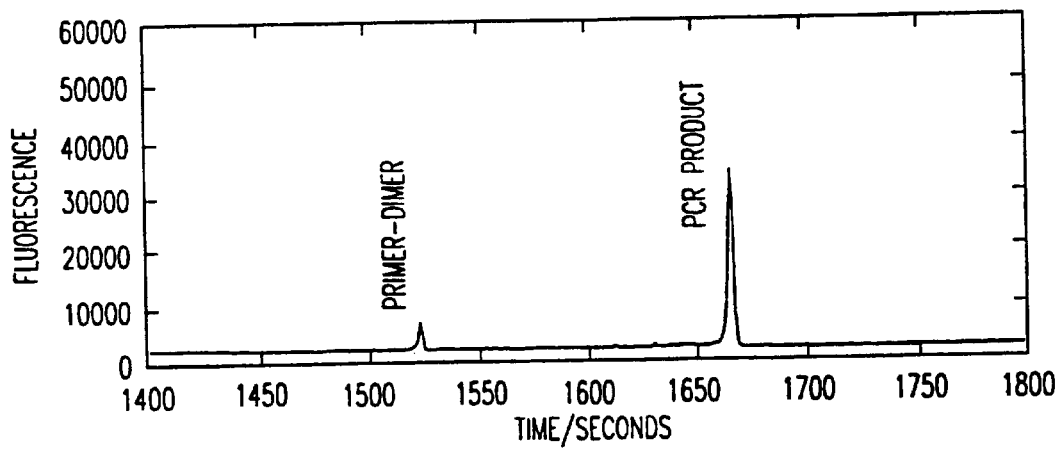
Figure 8C:
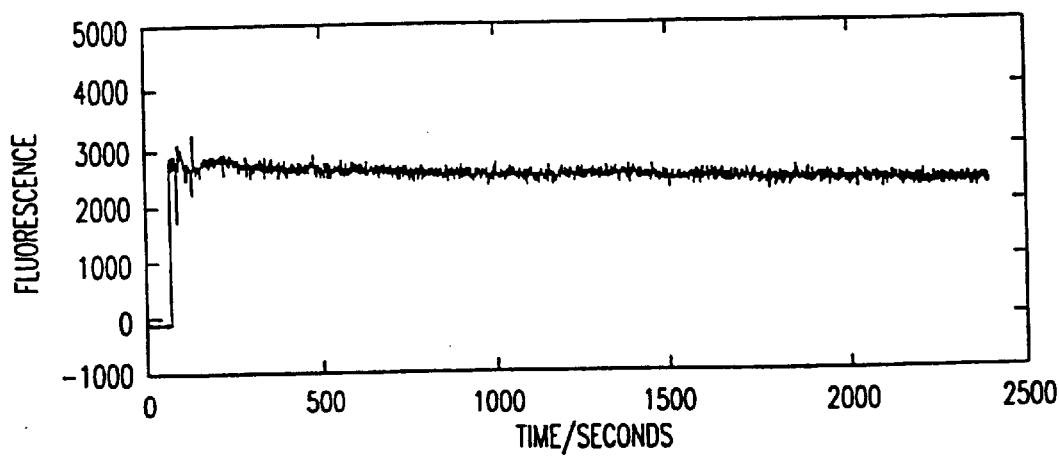

FIG. 8 shows a comparison of the chip amplified reaction and positive and negative control amplifications performed in the Perkin-Elmer instrument. Results indicate a comparable amplification efficiency for the chip reaction compared with the control. Despite the 10 fold dilution of the chip reaction, peak heights are observed to be similar since samples were electrokinetically injected onto the capillary (proportional increase in stacking). Negative control reactions were identical to positive controls, except that target DNA was not added to the amplification reaction. As a further control, the unamplified positive control reactions were injected onto the capillary. No peak was observed for these reactions either (data not shown).

Having described preferred embodiments of the invention with reference to the accompanying drawings, it is to be understood that the invention is not limited to those precise embodiments, and that various changes and modifications may be effected therein by one of skill in the art without departing from the scope or spirit of the invention as defined in the appended claims.

We claim:

1. An integrated microvolume device for performing polymerase chain reaction and electrophoresis, the device comprising: at least one reaction chamber, the reaction chamber comprising
   two planar members coupled together at at least one point, wherein one planar member has a thickness of up to about 1 mm and is thicker than the other planar member;
   a cavity disposed within the planar members;
   at least one aperture in communication with the cavity to permit the introduction and withdrawal of fluids therefrom;
   a thin film metal heater disposed within the cavity; and
   a thermocouple having a temperature-sensing junction disposed adjacent to the cavity;
   an electrophoresis capillary; and
   channels in fluid communication with the cavity and the electrophoresis capillary.

2. The device as defined in claim 1, wherein the surface of one of the planar members is coated with a passivating agent.

3. The device as defined in claim 2, wherein the passivating agent is a linear polyacrylamide.

4. The device as defined in claim 1, wherein the cavity contains an amplification buffer and Bovine Serum Albumin.

5. The device as defined in claim 4, further comprising nucleic acid, a nucleic acid polymerase, and amplification primer sequences for performing polymerase chain reaction disposed within the cavity.

6. The device as defined in claim 1, wherein the thin film metal heater is a thin film resistive heater.

7. The device as defined in claim 1, wherein the thin film heater comprises a thin film heater deposited by thin film deposition.

8. The device as defined in claim 1, wherein the thin film metal heater is covered with an insulating layer.

9. The device of claim 1, wherein the thermocouple is a thin film chrome/gold thermocouple.

10. The device as defined in claim 1, wherein the thermocouple is disposed between the thin film metal heater and one of the planar members.

11. The device as defined in claim 1, wherein the thermocouple is covered with a dielectric layer.

12. The device as defined in claim 1, wherein the thermocouple is disposed within the cavity.

13. The device as defined in claim 1, wherein the planar members comprise at least one material independently selected from the group consisting of soda lime glass, borofloat glass, plastic, and PMMA.

14. The device as defined in claim 1, further comprising an oligonucleotide array, the oligonucleotide array including a substrate having a plurality of positionally distinct oligonucleotide probes coupled to a surface of one of the planar members.

15. The device as defined in claim 1, wherein the thermocouple further comprises a reference junction.

16. The device as defined in claim 15, wherein the sensing junction comprises a first gold film adjoined to a chromium film, and the reference junction comprises a chromium film adjoined to a second gold film.

17. The device as defined in claim 1, further comprising a thermocycling program which receives data from the thermocouple and controls the temperature of the thin film heater in response to the data.

18. An integrated microvolume device for performing polymerase chain reaction and electrophoresis, the device comprising at least one reaction chamber, the reaction chamber comprising
   two generally planar members coupled together in an overlapping relationship, each planar member having a cavity defining a chamber therebetween, wherein one planar member has a thickness of up to about 1 mm and is thicker than the other planar member, and wherein wherein at least one of the planar members has an elongated aperture in flow communication with the chamber to permit the introduction and withdrawal of fluids therefrom;
   a thin film heater disposed within the chamber; and a thermocouple having a temperature-sensing junction disposed in one of the planar members, being positioned so as to sense the temperature of a reaction occurring within the chamber an electrophoresis capillary; and channels in fluid communication with the chamber and the electrophoresis capillary.

19. The device of claim 18, wherein the surface of one of the planar members is coated with a passivating agent.

20. The device as defined in claim 19, wherein the passivating agent is a linear polyacrylamide.

21. The device of claim 18, wherein the thermocouple is a thin film chrome/gold thermocouple.

22. The device of claim 18, wherein the thermocouple is disposed between the thin film metal heater and one of the planar members.

23. The device of claim 18, wherein the thermocouple is covered with a dielectric layer.

24. The device of claim 18, wherein the thermocouple is disposed within the chamber.

25. The device of claim 18, wherein the planar members comprise at least one material independently selected from the group consisting of soda lime glass, borofloat glass, plastic, and PMMA.

26. The device as defined in claim 18, further comprising an oligonucleotide array, the oligonucleotide array including a substrate having a plurality of positionally distinct oligonucleotide probes coupled to a surface of one of the planar members.

27. The device of claim 18, wherein the thermocouple further comprises a reference junction.

28. The device of claim 27, wherein the sensing junction comprises a first gold film adjoined to a chromium film, and the reference junction comprises a chromium film adjoined to a second gold film.

29. The device as defined in claim 18, further comprising a thermocycling program which receives data from the thermocouple and controls the temperature of the thin film heater in response to the data.

* * * * *

UNITED STATES PATENT AND TRADEMARK OFFICE
CERTIFICATE OF CORRECTION

| | |
|---|---|
| PATENT NO. | : 6,261,431 B1 |
| APPLICATION NO. | : 09/221436 |
| DATED | : July 17, 2001 |
| INVENTOR(S) | : Mathies et al. |

It is certified that error appears in the above-identified patent and that said Letters Patent is hereby corrected as shown below:

Col. 1, line 4, after the title, please add the following paragraph:

GOVERNMENT INTEREST

This invention was made with government support under grant number HG01399 awarded by the National Institute of Health. The government has certain rights in the invention.

Signed and Sealed this

Twenty-second Day of September, 2009

David J. Kappos
*Director of the United States Patent and Trademark Office*